US008399658B2

(12) United States Patent
Hengstermann et al.

(10) Patent No.: US 8,399,658 B2
(45) Date of Patent: Mar. 19, 2013

(54) METHOD FOR ISOLATION OF LAUROLACTAM FROM A LAUROLACTAM SYNTHESIS PROCESS STREAM

(75) Inventors: Axel Hengstermann, Senden (DE); Ralf Meier, Dortmund (DE); Daniel Demicoli, Essen (DE); Martin Roos, Haltern am See (DE); Bernd Guenzel, Schermbeck (DE); Frank Huebner, Ober-Ramstadt (DE)

(73) Assignee: Evonik Degussa GmbH, Essen (DE)

( * ) Notice: Subject to any disclaimer, the term of this patent is extended or adjusted under 35 U.S.C. 154(b) by 144 days.

(21) Appl. No.: 12/951,289

(22) Filed: Nov. 22, 2010

(65) Prior Publication Data

US 2011/0124855 A1    May 26, 2011

(30) Foreign Application Priority Data

Nov. 20, 2009  (DE) .................. 10 2009 046 910

(51) Int. Cl.
C07D 201/16    (2006.01)
(52) U.S. Cl. ........................................ 540/451
(58) Field of Classification Search .................. 540/451
See application file for complete search history.

(56) References Cited

U.S. PATENT DOCUMENTS

| 7,495,129 B2 | 2/2009 | Balduf et al. |
| 2002/0010329 A1 | 1/2002 | Shimazu et al. |
| 2003/0180203 A1 | 9/2003 | Furuya |
| 2009/0088567 A1 | 4/2009 | Hengstermann et al. |
| 2009/0306367 A1 | 12/2009 | Roos et al. |
| 2010/0063323 A1 | 3/2010 | Baumgarten et al. |
| 2010/0324283 A1 | 12/2010 | Ishihara et al. |

FOREIGN PATENT DOCUMENTS

| EP | 2 123 635 A1 | 11/2009 |
| EP | 2 241 552 | 10/2010 |
| JP | 2002-3470 | 1/2002 |
| JP | 2002-3472 | 1/2002 |
| JP | 2002-102603 | 4/2002 |
| JP | 2002-193928 | 7/2002 |
| JP | 2004-59554 | 2/2004 |
| JP | 2008-308461 | 12/2008 |
| JP | 2009/185005 | 8/2009 |
| WO | WO 2007/125002 A1 | 11/2007 |
| WO | 2008/096873 | 8/2008 |

OTHER PUBLICATIONS

European Search Report issued Feb. 18, 2011, in Patent Application No. 10186481.7 with English translation of category of cited documents.
U.S. Appl. No. 12/438,295, filed Feb. 20, 2009, Kuppinger et al.
Thomas Schiffer, et al. "Cyclododecanol, Cyclododecanone, and Laurolactam" 2005 wiley-VCH Verlag GmbH & Co. KGaA, Weinheim.
Letter from Keisen associates, Omori & Yaguchi USA dated Oct. 24, 2012, 3 pages.

*Primary Examiner* — Bruck Kifle
(74) *Attorney, Agent, or Firm* — Oblon, Spivak, McClelland, Maier & Neustadt, L.L.P.

(57) ABSTRACT

A process for purifying laurolactam by means of integrated connection of distillation and crystallization is provided. The crystallization is performed as a solution or melt crystallization. The process reduces thermal stress applied to the laurolactam stream and improved yields are obtained. Raw materials are recovered and recycled in the production sequence.

15 Claims, 1 Drawing Sheet

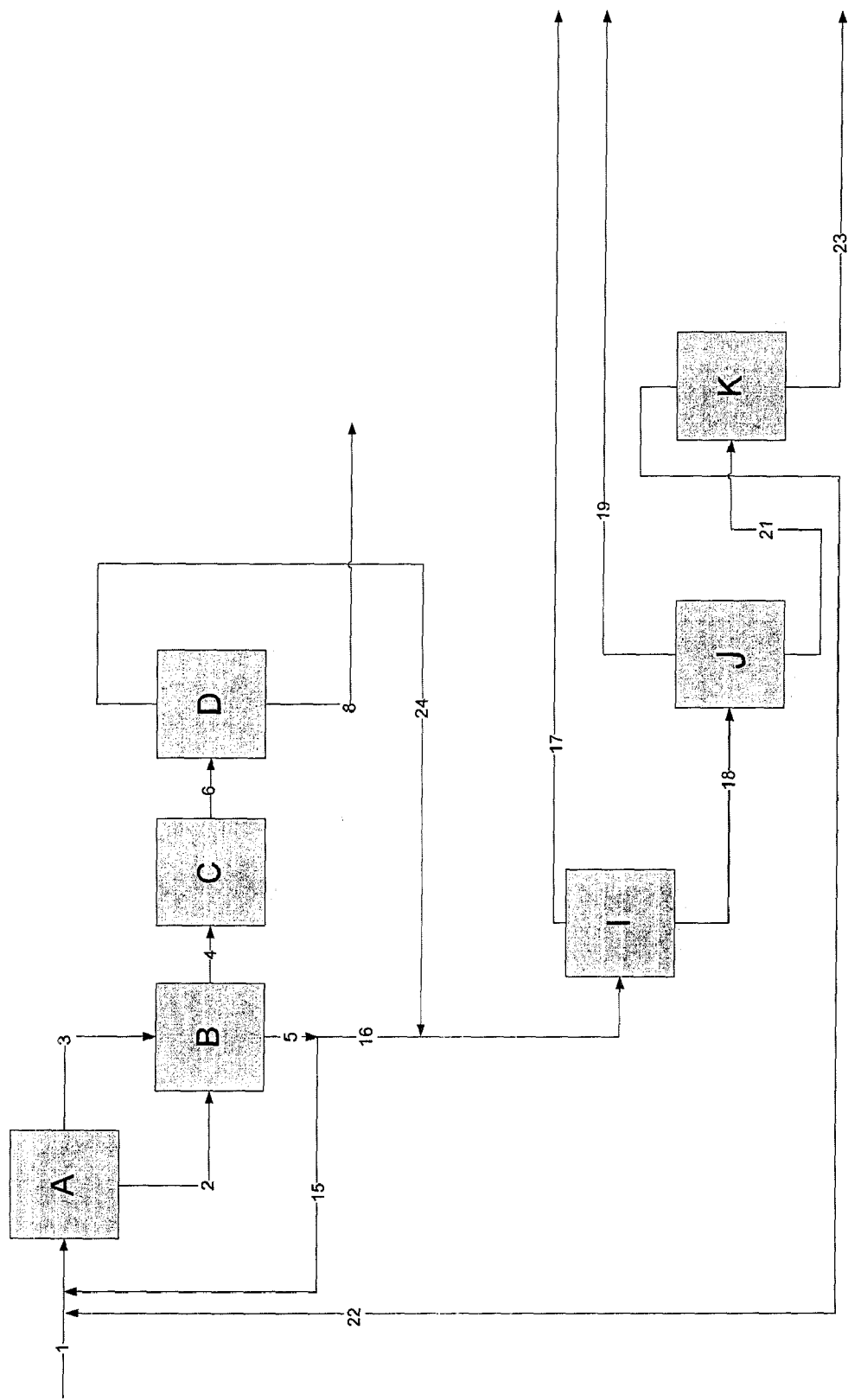

METHOD FOR ISOLATION OF LAUROLACTAM FROM A LAUROLACTAM SYNTHESIS PROCESS STREAM

CROSS REFERENCE TO RELATED APPLICATIONS

This application claims priority to prior German Application 102009046910.9-44, filed Nov. 20, 2009, the disclosure of which is incorporated herein by reference.

BACKGROUND OF THE INVENTION

1. Field of the Invention

The present invention is directed to a process for purifying laurolactam by an integrated connection of distillation and crystallization. The crystallization may be performed as a solution or melt crystallization. The stream from which the laurolactam is isolated may comprise, in addition to the laurolactam, at least one component other than laurolactam which may have a lower or higher boiling point than laurolactam. More specifically, the stream may be a laurolactam synthesis stream comprising laurolactam, a mother liquor, synthesis starting materials and low, mid- and high boiling fractions.

2. Description of the Related Art

Laurolactam is typically purified by means of a multistage distillation in which secondary components with higher and lower boiling points are removed from the laurolactam. Conventionally, such distillation processes employ application of reduced pressure, due to the high boiling point of laurolactam. As a result of thermal stress on a laurolactam mixture in conventional purification methods, partial thermal decomposition of the laurolactam, resulting in overall yield reduction and high production cost, is experienced.

The "conventional" process for synthesis and isolation of laurolactam is described in Ullmann's Encyclopedia of Industrial Chemistry (2005 Wiley-VCH Verlag GmbH & Co. KGaA, Weinheim 10.1002/14356007.a08_201), in the article: "Cyclododecanol, Cyclododecanone, and Laurolactam" by Thomas Schiffer and Georg Oenbrink

BRIEF DESCRIPTION OF THE DRAWING

The FIGURE shows a flow diagram of an embodiment of the present invention.

DETAILED DESCRIPTION OF THE INVENTION

The present invention is directed to a method for the isolation and purification of laurolactam which provides the following benefits:
- early removal of laurolactam in the workup process
- reduction in the thermal product stress by reducing the number of thermal separation steps necessary
- reduction in the thermal stress via lowering the process temperature needed
- recovery of all materials of value present in the stream, such as reactants and/or solvents
- removal and discharge of the components other than target product/reactants and solvents.

This and other objects have been achieved by the present invention, the first embodiment of which provides a method for isolation and purification of laurolactam from a laurolactam synthesis process stream, comprising:

cooling the synthesis process stream comprising laurolactam, a mother liquor, synthesis starting materials and low, mid- and high boiling fractions to a temperature wherein only the solubility limit of the laurolactam is exceeded, to selectively crystallize the laurolactam from the mother liquor;

separating the crystallized laurolactam from the mother liquor in a downstream solid-liquid separation; and sending the mother liquor from which the crystallized laurolactam is separated to a multistage distillation sequence;

wherein solvent and reactant components of the laurolactam synthesis process stream are recovered.

In further preferred embodiments, the selective crystallization is a solution cooling crystallization, preferably a flash cooling crystallization.

In a second embodiment, the present invention provides a method for isolation of laurolactam from a laurolactam synthesis process stream, comprising:

increasing the temperature of the synthesis process stream comprising laurolactam, a mother liquor, synthesis starting materials and low, mid- and high boiling fractions by conducting the synthesis process stream through a heat exchanger;

decompressing the heated synthesis process stream in a flash vessel to obtain a vapor phase and a low-boiling fraction which comprises laurolactam;

sending the vapor phase to a distillative separating sequence to produce a fraction of the vapor phase comprising laurolactam;

combining the low-boiling fraction and the vapor phase fraction comprising laurolactam; and melt crystallizing the combined fractions.

According to the method of the invention, a stream comprising laurolactam which arrives from the synthesis and comprises laurolactam, and further components may be first cooled such that, in a selective manner, by solution cooling crystallization, only the solubility limit of laurolactam is exceeded and laurolactam is selectively crystallized out and removed from the mother liquor in a downstream solid-liquid separation, and the mother liquor is subsequently sent to a multistage distillation sequence.

The crystallization may be performed as a solution crystallization, as a solution cooling crystallization or flash cooling crystallization.

For a stream consisting of laurolactam and components different therefrom, the following workup sequence according to the claims has been found. By way of example, the process is described by the appended flow diagram (FIGURE) and described with the following stream composition component designations:

LB—low boilers
LM—solvent
MB1—medium boiler fraction 1
CDON—cyclododecanone as a reactant of the synthesis
MB2—medium boiler fraction 2
HB—high boilers
LL—laurolactam The flow diagram (FIGURE) is merely illustrative and is not intended to restrict the process. The stream 1 which arrives from a synthesis sequence and contains laurolactam, solvent, CDON and components different therefrom is fed together with the mother liquor recycle stream 15 which contains laurolactam, solvent, CDON and components different therefrom, and the distillate 22 of an evaporation apparatus K, comprising predominantly laurolactam, to a flash cooling crystallization A with a temperature of at least 75° C., preferably at least 80° C. and more preferably at least 85° C. The reduced vacuum in the flash cooling crystallization A establishes a corresponding boiling equilibrium. The amount of heat Q resulting from the temperature difference between inlet stream and boiling temperature leads to evaporation of the volatile constituents and to a lowering of the temperature according to the boiling equilibrium. As a result of the superimposition of the evaporation and temperature reduction effects, the solubility limit of laurolactam is exceeded and laurolactam crystallizes out. At the crystallizer outlet, a temperature of not more than 70° C., preferably lower, preferably a temperature of approx. 65° C., is established. The suspension 2 is conducted out of the flash cooling crystallization A to the solid-liquid separation B. The suspension is separated therein into mother liquor 5 and solid comprising predominantly laurolactam 4. The moist solid 4 may be freed of the adhering secondary components with condensed distillate 3 comprising predominantly solvent. The mother liquor obtained and the laden wash liquor are combined to give stream 5. A substream 15 is introduced back into the flash cooling crystallization A to increase the yield and adjust the solids content.

The washed moist solid 4 is fed to a melting unit C. The melting unit C is operated at a temperature above the melting point of laurolactam. The molten stream 6 is sent to a flash stage D. At the top of the flash stage, a vapour stream 24 is removed and supplied to a distillative workup sequence including sequences I, J and K. The bottom stream 8 containing on-spec laurolactam is removed and leaves the process.

Streams 16 and 24 are sent to distillative removal of solvent and secondary components, consisting of sequences I, J and K.

The crystallization A may be performed as a flash cooling crystallization. This means that the amount of heat Q present in the feed stream 1+15+22 is used for partial evaporation of the solvent 3. In order that the solvent evaporates, according to the vapour pressure of the feed stream, a corresponding pressure and hence a corresponding internal crystallizer temperature are established. As a result of the controlled evaporation of the solvent 3 and the cooling of the solution, the solubility limit of laurolactam is exceeded and laurolactam crystallizes from the solution. An efficient connection allows the oversaturation needed for crystallization to be adjusted to a moderate level. The evaporative cooling may allow direct heat exchange to be dispensed with completely in the crystallizer, such that encrustation tendencies of heat-transferring surfaces may be reduced significantly. The corresponding amount of heat is removed via the top condenser.

The solids obtained in the crystallization in stream 2 may be removed from the mother liquor 5 in a downstream solid-liquid separation B. To remove the adhering mother liquor from the solid surface, the solids may be washed with an appropriate wash liquid. To wash the solid, several wash liquids, in which laurolactam has a low solubility have been identified. Ideally, a wash liquid which may already be present in the process, which dissolves the adhering components and which can be recovered may be used. In this context, one possible washing agent identified has been the solvent 3 removed in the crystallization step A.

The moist crystals 4 may be freed of the adhering washing agent in a subsequent drying step C and D. It has been found that it may be advantageous in apparatus terms to melt laurolactam in a melter C and to remove it from the solvent 24 by conventional flash evaporation D. Laurolactam is entrained in the flash vapors and such entrainment leads to coverage and encrustation of installed heat exchange surfaces and therefore requires a specific condensation system known to those skilled in the art for stream 24. The installed medium boiler removal I and J may be configured in an integrated manner as a dividing wall column, the advantages of which are sufficiently well known to those skilled in the art. At the top of the column I/J, the medium boilers 17 are removed with a lower boiling point than the CDON product of value present. The installed dividing wall within the column I/J allows residual laurolactam with the high boilers present in 18 to be removed via stream 21 at the bottom of the column. The CDON present and the medium boilers having a higher boiling point than CDON in 18 may each be removed within the permissible specification limits via a side draw 19 on the opposite side of the dividing wall column and the CDON sent to the laurolactam synthesis feed stream.

The bottom product 21 rich in laurolactam and high boilers is sent from the medium boiler distillation I/J for removal of high boilers to a further workup step K. This consists of an evaporation apparatus for high-viscosity fluids which is sufficiently well known to a person skilled in the art. The high-boiling components are discharged here via the bottom stream 23. The condensed vapors 22 which comprise the majority of the laurolactam originally present in the bottom product of the medium boiler distillation I/J may be recycled into the workup sequence to increase the yield. The recycling may be effected into the crystallization A.

The process detailed, according to the claims for working up laurolactam and for recovering the components of value present, such as solvent and reactant, may exhibit the following advantages over a conventional distillation process:

A majority (greater than 80%, preferably greater than 85% and more preferably greater than 90%) of the material of value can be removed via the crystallization merely by cooling of the stream.

The main fraction of the laurolactam produced does not pass through any hot separation steps in which there may be thermal stress or decomposition.

Reduction of the high boiler content (laurolactam) allows the bottom temperature of the dividing wall column to be operated at a moderate temperature level The combination of crystallization and distillation reduces the number of thermal separating operations necessary to a minimum.

The low thermal stress on the laurolactam allows the formation of polymers from laurolactam to be reduced, such that the feedstock factor is improved over the workup sequence.

The laurolactam removed in the crystallization has a purity of >99%.

Having generally described this invention, a further understanding can be obtained by reference to a specific example which is provided herein for purposes of illustration only and is not intended to be limiting unless otherwise specified.

Working Example:

A laurolactam-containing stream was introduced at 1.5 kg/h at a temperature of 90° C. into a stirred guide tube crystalliser with an internal, temperature of 35° C. and a liquid volume of 3.21. The pressure level of the crystalliser was approx. 0.05 bar absolute (abs). The stream comprised, as well as 20% by weight of laurolactam (LL) and approx. 77.5% by weight of solvent (LM), 2.5% by weight of secondary components other than LL and LM. The stream supplied was supplied to the crystalliser via a cross-sectional constriction with a pressure greater than the boiling pressure of solvent. As soon as the stream entered the liquid volume, an equienthalphic mass of solvent evaporated, approx. 0.25 kg/h. The evaporation enthalphy required was removed from the liquid system by lowering of the temperature. The evaporation of the solvent oversaturated the system with LL. The oversaturation was degraded by controlled crystal growth on the solid surface present. The mean residence time of the liquid-solid phase is approx. 2.5 h. The suspension obtained, approx. 1.25 kg/h, is removed batchwise in 10 min cycles.

The suspension was introduced into a conventional laboratory filter centrifuge. The mother liquor (approx. 0.85 kg/h) was separated therein from the solid moist target product (approx. 0.4 kg/h), the solid laurolactam. To raise the product quality, the solids were washed with cold (preferably with a temperature less than 65° C.) solvent (approx. 0.4 kg/h). This achieved washing of the solid surface, which removed undesired secondary components. The moist solid was dried at 90° C. in a drying cabinet under reduced pressure (100 mbar). On completion of drying, 0.275 kg/h of solids remained. This corresponds to a yield of 91.7% laurolactam.

Solvent Selection

For the process detailed, preference was given to using hydrocumene as the solvent. Alternatively, it may also be possible to use the solvents listed below. It may be possible here to use different components or mixtures of components, for example hydrocumene (HC), cyclododecanone (CDON), cyclododecatriene (CDT), toluene, cycloheptane, cyclooctane (COA), cyclononane, cyclodecane, cyclododecane, vinylcyclohexane (VCH) or ethylcyclohexane (ECH), dimethylcyclohexane, tert-butylcyclohexane. In addition, combinations of the solvents listed may be possible, since the eutectic behaviour, i.e. the melting point depression, of the mixtures can be exploited advantageously here. A lowering of the melting point of the dissolution medium (mixture of different solvents) reduces the apparatus complexity, since it would be possible to dispense with complex trace heating.

Numerous modifications and variations on the present invention are possible in light of the above teachings. It is therefore to be understood that within the scope of the appended claims, the invention mat be practiced otherwise than as specifically described herein.

The invention claimed is:

1. A method for isolation and purification of laurolactam from a laurolactam synthesis process stream, comprising:
    cooling the synthesis process stream comprising laurolactam, a mother liquor, synthesis starting materials and low, mid- and high boiling fractions to a temperature wherein only a solubility limit of the laurolactam is exceeded, to selectively crystallize the laurolactam from the mother liquor;
    separating the crystallized laurolactam from the mother liquor in a downstream solid-liquid separation; and
    sending the mother liquor from which the crystallized laurolactam is separated to a multistage distillation sequence;
    wherein components of the laurolactam synthesis process stream are recovered.

2. The process according to claim 1, wherein
the selective crystallization is a solution crystallization.

3. The process according to claim 2, wherein
the solution crystallization is a solution cooling crystallization.

4. The process according to claim 3, wherein
the solution cooling crystallization comprises a flash cooling crystallization.

5. The process according to claim 1, wherein
the selective crystallization and separation remove more than 80% of the laurolactam in the laurolactam synthesis process stream from the stream.

6. The process according to claim 1, further comprising:
washing the separated crystallized laurolactam with a wash liquid to remove mother liquor adhering to the crystallized laurolactam.

7. The process according to claim 6, wherein
the wash liquid comprises at least one selected from the group consisting of hydrocumene, cyclododecanone, cyclododecatriene, toluene, cycloheptane, cyclooctane, cyclononane, cyclodecane, cyclododecane, vinylcyclohexane, ethylcyclohexane, dimethylcyclohexane and tert-butylcyclohexane.

8. The process according to claim 6,
wherein the wash liquid is hydrocumene.

9. The process according to claim 1, further comprising:
drying the separated crystallized laurolactam.

10. The process according to claim 3, wherein
a purity of the separated crystallized laurolactam is greater than 99%.

11. The process according to claim 1, further comprising:
distilling the synthesis process stream comprising laurolactam before the cooling to a temperature where only a solubility limit of the laurolactam is exceeded.

12. The process according to claim 11, wherein
the distillation of the synthesis process stream comprises:
a distillative separating sequence in which the low boilers present are distilled overhead with solvent, and bottoms from the low boiler column which comprise laurolactam are treated as the synthesis process stream.

13. The process according to claim 12, wherein
the crystallization is a solution cooling crystallization.

14. The process according to claim 13, wherein
the solution cooling crystallization is a flash cooling crystallization.

15. A method for isolation of laurolactam from a laurolactam synthesis process stream, comprising:
    increasing the temperature of the synthesis process stream comprising laurolactam, a mother liquor, synthesis starting materials and low, mid- and high boiling fractions by conducting the synthesis process stream through a heat exchanger;
    decompressing the heated synthesis process stream in a flash vessel to obtain a vapor phase and a low-boiling fraction which comprises laurolactam;
    sending the vapor phase to a distillative separating sequence to produce a fraction of the vapor phase comprising laurolactam;
    combining the low-boiling fraction and the vapor phase fraction comprising laurolactam; and
    melt crystallizing the combined fractions.

* * * * *